US007612116B2

(12) United States Patent
Paris (10) Patent No.: US 7,612,116 B2
(45) Date of Patent: Nov. 3, 2009

(54) USE OF THICKENING AGENTS FOR PRODUCING SOFT CAPSULES AND FILM PRODUCTION METHOD

(76) Inventor: Laurence Paris, 24, rue du Progrès, 03600 Commentry (FR)

( * ) Notice: Subject to any disclaimer, the term of this patent is extended or adjusted under 35 U.S.C. 154(b) by 125 days.

(21) Appl. No.: 10/539,100

(22) PCT Filed: Dec. 16, 2003

(86) PCT No.: PCT/FR03/00374

§ 371 (c)(1),
(2), (4) Date: Dec. 16, 2002

(87) PCT Pub. No.: WO2004/060356

PCT Pub. Date: Jul. 22, 2004

(65) Prior Publication Data

US 2006/0292212 A1    Dec. 28, 2006

(30) Foreign Application Priority Data

Dec. 16, 2002   (FR)   ................... 2002015905

(51) Int. Cl.
C08J 3/03    (2006.01)
C08J 3/09    (2006.01)

(52) U.S. Cl. ................. 516/105; 516/106; 516/107; 516/108; 516/109; 516/98

(58) Field of Classification Search ................. 516/105, 516/106, 107, 108, 109, 98
See application file for complete search history.

(56) References Cited

U.S. PATENT DOCUMENTS

| 4,333,461 | A | * | 6/1982 | Muller | ................... 604/368 |
| 4,624,868 | A | * | 11/1986 | Muller | ................... 427/384 |
| 6,235,312 | B1 | * | 5/2001 | Hobbs et al. | ................ 424/484 |
| 6,331,205 | B1 | * | 12/2001 | Paris et al. | ................ 106/205.9 |
| 6,586,590 | B1 | * | 7/2003 | Renn et al. | ................... 536/128 |
| 6,800,663 | B2 | * | 10/2004 | Asgarzadeh et al. | ........ 516/108 |
| 6,908,885 | B2 | * | 6/2005 | Bengs et al. | ................ 504/366 |
| 2002/0019447 | A1 |  | 2/2002 | Renn et al. |  |

FOREIGN PATENT DOCUMENTS

| FR | 2713931 | * | 6/1995 |
| FR | 2 767 070 | A | 1/1999 |
| GB | 2 067 214 | A | 7/1981 |
| WO | WO 01/07507 | A | 2/2001 |

OTHER PUBLICATIONS

English translation of FR 2,713,931, Jun. 23, 1995.*
"Gelatin-Free System for Soft/Hard Capsules Containing Gellan Gum" Kenneth Mason Publications, Hampshire, GB, No. 332, pp. 908, Dec. 1, 1991.

* cited by examiner

Primary Examiner—Douglas M C Ginty
(74) Attorney, Agent, or Firm—Paul & Paul (57) ABSTRACT

The invention concerns the gelatinization of viscous aqueous or hydroalcoholic liquid components, buffered or not, intended for the production of films for the manufacture of soft capsules. These compositions are notable in particular in that gelatinization thereof is obtained extemporaneously starting with thickening agents that exhibit the unique property of gelatinizing instantly upon contact with complexing solutions, the elasticity of the films being obtained by introducing or not introducing a plasticizing agent, decomposition thereof being controlled by incorporating or not incorporating a surfactant or a polysaccharide, and preservation thereof being ensured or not ensured by the addition of preservatives, thus allowing it to contain oily and/or aqueous solutions. The invention also concerns a method for manufacturing films for such capsules, which comprises gelatinization of said films by applying a complexing agent to the mass by spraying and/or by immersion. Applications: pharmaceuticals, cosmetics, and foods.

26 Claims, 4 Drawing Sheets

USE OF THICKENING AGENTS FOR PRODUCING SOFT CAPSULES AND FILM PRODUCTION METHOD

APPLICABILITY OF THE INVENTION

The present invention refers to the pharmaceutical, cosmetic, and dietetic fields, and more specifically concerns the production of films for obtaining soft capsules from substances having thickening properties. The invention also concerns a method for obtaining such films and said soft capsules.

DESCRIPTION OF THE EXISTING ART

At present, the casing of soft capsules is in most cases based on gelatin, which is used either in pure form (gel capsules) or in combination with various substances (glycerin, sorbitol, etc.). Because of potential problems that may arise regarding the origin of the gelatin, which in most cases derives from bovine bone, "mad cow disease" or bovine spongiform encephalitis (BSE) makes it crucially important to be able to replace such a product.

Numerous substances have been studied with the goal of replacing gelatin in soft capsules. In most cases, these substances are defined as gelatinizing agents that yield colloidal solutions. "Gelatinizing" is understood to refer to substances that, after hot solubilization and cooling, yield a solid mass having a more or less elastic structure identical to that of gelatin. Aside from the fact that they yield a gelatinous mass upon cooling, however, these substances must meet three essential criteria for the production of soft capsules, i.e. they must:

- be film-producing, i.e. said substances must form, by cooling and casting, continuous films having a thickness from 0.1 mm to 10 mm and more;
- yield a thermoreversible structure, i.e. said substances instantly become liquid again in response to heat, and conversely gelatinize very quickly in the presence of cold. This parameter is fundamental in terms of obtaining a perfect weld between two films subjected to the action of pressure and heat;
- yield an elastic solid structure, i.e. said gelatinized substances deform in response to a force such as a pressure or traction, and return to their initial shape after application of the force ceases.

Of all the substances exhibiting these characteristics, such as the alginates, certain gums such as xanthan gums, agar-agar, iota carrageenans, kappa carrageenans, etc., very few have yielded satisfactory results in terms of the parameters required in the finished product, among them the disaggregation time of the soft capsule. According to the standards established by various Pharmacopeias, a soft capsule must exhibit a maximum disaggregation time of 30 minutes. In the case of soft capsules made of gelatin, this time is on the order of 5 to 7 minutes at 37° C. in water. In most cases, the gelatin substitutes yield values well above 15 minutes, and even exceed 30 minutes. A number of patents have nevertheless been acquired in the field of soft capsules using the aforesaid substances, used either as the only gelatinizing agent or in combination with a second gelatinizing agent or even a thickening agent.

One of the substance categories with the most patents is that of the carrageenans, in particular the iota and kappa carrageenans, both of which exhibit gelatinizing properties. Only the iota carrageenans yield an elastic structure like gelatin. The kappa carrageenans, aside from the fact that they yield a brittle rather than an elastic solid mass, exhibit another drawback, that of a substantial re-release of water from the films that are formed. This results in significant shrinkage of the films over time, and hence poor stability of the finished products. These substances have given rise to a certain number of patents in the field of soft capsules, such as:

- JP 09025228, JP 62289530, and U.S. Pat. No. 5,342,626, in which the carrageenans are combined with another gelatinizing agent, and their concentration in the medium never exceeds 5%. In addition, U.S. Pat. No. 5,342,626 and JP 60012943 mention the use of kappa carrageenans.
- PCT 00/10530 (Banner) mentions the use of kappa carrageenans as the only gelatinizing agent, but in a concentration in the medium greater than 5%.
- FR 2 767 070 and U.S. Pat. No. 6,331,205 mention the use of iota carrageenans, also used at concentrations greater than 5%.

Of all these patents, only FR 2 767 070 and U.S. Pat. No. 6,331,205 have resulted in industrial implementation. This is because iota carrageenans at high concentration do behave like gelatin, except that the temperature parameters for working the material differ. Disaggregation times are between 10 and 15 minutes at 37° C. in water, depending on the ingredients incorporated into the film. These values are entirely acceptable in the pharmaceutical field.

Use of these substances does involve one drawback during the manufacturing process: in order to prevent the preparation from solidifying, it must be kept at a temperature higher than its gelatinization point. In the case of the carrageenans, the temperature must be kept between 90° C. and 100° C. For gelatin, it is kept between 50° C. and 70° C.

A second category of substances has been tested, but more particularly in the area of hard capsules. These are the so-called "thickening" substances, which yield pseudo-colloidal solutions. "Thickening" must be understood to mean substances that, whether hot or cold and at low or high concentration, increase the viscosity of the medium in which they are dissolved, although without producing a gelatinous structure when cold or after cooling, as in the case of gelatin. These substances therefore cannot a priori be used at all in the field of soft capsules, since formation of a solid structure when cold does not occur. These substances are certainly regarded in most cases as film-producing agents. But in the present case, the films are obtained by the evaporation of water or of a solvent, and they have a thickness expressed in micrometers. In addition to their thickening properties, these substances are also widely used in tablet coating films. There are many such substances, belonging to the following classes:

- starches and their derivatives;
- celluloses and their derivatives;
- gums such as guar gum, carob bean gum, gum arabic, etc.

They are also widely used as gelatin substitutes in the context of gel capsule production. Such is the case for hydroxypropylmethylcellulose, which is found in all so-called "vegetable origin" gel capsules and has generated numerous patents such as U.S. Pat. Nos. 5,756,123, 4,026,986, and 5,431,917, and EP 0 592 130.

PCT 00/18835 (Warner Lambert) proposes hydroxypropyl starch for the production of gel capsules and, to a lesser degree, for soft capsules. But it is used in combination with a very small proportion of a gelatinizing agent of vegetable origin (kappa carrageenans). The combination of these two substances makes possible instant gelatinization of the hydroxypropyl starch mass by cooling upon emergence from the bath, thus reproducing the gelatin mechanism.

In the field of soft capsules, only the "Swiss caps" patents PCT 01/37817 and EP 1 103 254 describe production thereof from these aforesaid substances, i.e. starch. The starch undergoes a heat treatment in the presence of adjuvants, however, resulting in the formation of so-called thermoplastic starches. This heat treatment is achieved by "cracking," i.e. under high pressure and high heat, the starch grains explode and combine with the adjuvants present in the medium. This kind of process utilizes special mixers called "extruders." Conventional mixers cannot in any circumstance permit a chemical reaction of this kind.

DESCRIPTION OF THE INVENTION

Aside from the "Swiss Caps" patent which utilizes a thickening agent, an intensive study of all the other patents relating to soft capsules without gelatin has not revealed any evidence of the use of a thickening agent as the only "gelatinized" component of the casing of soft capsules, which is the object of the present invention.

For that purpose, the viscous aqueous or hydroalcoholic liquid components, buffered or not, intended for the production of films for the manufacture of soft capsules according to the present invention are notable in that gelatinization thereof is obtained extemporaneously starting with thickening agents that exhibit the unique property of gelatinizing instantly upon contact with complexing solutions, the elasticity of the films being obtained by introducing or not introducing a plasticizing agent, decomposition thereof being controlled by incorporating or not incorporating a surfactant or a polysaccharide, and preservation thereof being ensured or not ensured by the addition of preservatives, thus allowing it to contain oily and/or aqueous solutions.

The object of the present invention is to replace the gelatin of soft capsules with materials belonging to the category of substances called thickeners, and to develop the respective method. According to a particularly advantageous characteristic of the invention, the requisite parameters of a solid, elastic, film-producing, and thermoreversible structure are obtained extemporaneously during casting of the film by the action of substances that bring about an instant gelatinization of said film, in contrast to the known patents in which this characteristic is sought beginning with manufacture of the encapsulation compound.

The films thus obtained, when cold, exhibit characteristics similar to a gelatin film, in particular with regard to thermoreversibility, elasticity, and disaggregation time, by the addition or not of ingredients promoting such parameters. No gelatinizer such as gelatin, iota or kappa carrageenans, xanthan gum, etc. is used in combination with the aforesaid thickening substances to produce the requisite properties described above.

The object of the present invention is therefore based on the fact that certain substances of natural origin have the property of gelatinizing instantly upon contact with certain aqueous and/or hydroalcoholic solutions having a greater or lesser concentration of ions. "Ions" are understood to be ionized elements such as hydrogen ions ($H^+$) defining acids, hydroxide ions ($OH^-$) defining bases;

anions and/or cations, defining salts (calcium, sodium, phosphates, etc.).

These solutions are defined as being "gelatinizing agents," and more particularly, in order to distinguish them in the context of the present invention, as "complexing agents."

The structures thus obtained are thermoreversible films, thus allowing the welding of two units in response to pressure and temperature during encapsulation of the active ingredients;

films that are more or less elastic depending on the gelatinizing or complexing agent used, and on the composition of said films, thus allowing filling by injecting a solution of active ingredient that is to be encapsulated.

The method that is likewise an object of the present invention exploits the advantage that these aforesaid substances of natural origin make it possible to work at a temperature much lower than their melting point, and at much higher concentrations of solid matter than the gelatinizers conventionally used, such as gelatin, the carrageenans (iota and kappa), and the gelatinizing compositions described in the various patents that were examined. The energy consumed during the encapsulation of active ingredients is thus reduced practically to nothing thanks to the absence of any need to keep the film-producing preparation heated in order to prevent it from gelatinizing in situ, as is often observed in the case of gelatin, the carrageenans, and the other gelatinizing compositions.

The aforesaid films that are the object of the present invention are obtained using thickening substances of vegetable origin or those that result from the metabolism of microorganisms and are very widely used in the food, agricultural, and pharmaceutical sector, which gelatinize instantly in contact with certain aqueous and/or hydroalcoholic solutions.

These thickening agents are generally highly soluble when cold, and belong to the class of polysaccharides containing on their polymer chain at least one molecule of glucose, galactose, mannose, and/or glucuronic acid, or a mixture of the three, and/or derivatives of the three.

These substances having an induced gelatinizing capability can be used alone or in combination with other non-gelatinizing excipients whose purpose is to improve the elasticity of the film;

enhance the welding of two films;

affect the disaggregation time of the casing;

ensure microbiological purity;

improve the final appearance of the capsule.

As a result, depending on the composition of the film, release of an active ingredient enclosed in such a capsule can vary between 5 minutes and 24 hours.

There are many thickening agents of vegetable origin, but not all yield gels on contact with complexing agents as defined above; or the gels that are formed do not exhibit the properties necessary for the production of soft capsules.

Some exhibit such properties when they are combined with other substances having gelatinizing properties. Such is the case for carob bean gum (a thickening agent), which in the presence of kappa carrageenans (a gelatinizing agent) will give rise to an elastic gel. In this case the carob bean gum plays the role of a plasticizer within the kappa-carrageenan gel, which normally has a brittle structure.

In other cases, a gel may form on contact with "gelatinizing agents," but it is not thermoreversible. Such is the case with the alginates, which will yield gels in the presence of calcium ions and in an acid medium; but those gels will not become liquid again in response to heat, as in the case of gelatin or the carrageenans. The same observation is made with pectins in an acid medium: a gel forms, but it is not thermoreversible.

The thickeners of vegetable origin are extracted from plants, fruits, and certain algae. These products are very widely used in the food, pharmaceutical, and cosmetics industries. Their principal role is to keep particles in suspension by thickening the liquid phase.

In addition to enhancing the viscosity of the medium, these aforesaid substances have the ability to solidify instantly when they are brought into contact with "gelatinizing agents."

These are:
gum arabic and its derivatives;
the lambda carrageenans.

Gum arabic is an exudation of the sap from the branches and trunk of various *Acacia* species (*vera, nilotica, senegalensis, verek, seyal*, etc.). It occurs as white tears; as large red pieces; or in irregular, angular, broken, shiny reddish-white pieces. Gum arabic is soluble in water. A 5% aqueous solution of gum acacia deriving from *Acacia verek* is dextrorotatory. The saturation concentration at 25° C. is 37 g per 100 g of water. Gum arabic is constituted, for the most part or entirely, by (−)-arabinose, (+)-galactose, (−)-rhamnose, and (+)-glycuronic acid. Gum arabic exists in nebulized form in order to facilitate solubilization. It is used in the food and pharmaceutical sectors as a suspension agent, emulsifier, and binder in the production of tablets. Gum arabic instantly yields a gel on contact with alcohol, sodium borate, and sodium silicate.

The carrageenans have been known for more than 600 years in medicine and the food sector, in particular because of their original property of gelatinizing milk by simple heating. They are polysaccharides—more or less sulfated galactose polymers. The carrageenans are extracted from various algae: *Chondrus crispus, Gigartina stellata, Gigartina acicularis, Gigartina skottsbergii, Gigartina pistillata, Gigartina chamissoi, Iridea, Eucheuma cottoni, Eucheuma spinosum*. The extraction method that is utilized results in different types of carrageenan whose basic skeleton is a chain of D-galactoses linked alternately at α-(1-3) and α-(1-4). The various qualities result from the quantity and location of the sulfate groups, and the presence or absence of a 3,6-anhydro bridge on the galactose linked at 1 and 4. The proportion of the various sulfate groups and of the 3,6-anhydrogalactose bridge has led to the isolation of different types of carrageenan. These are the iota, kappa, lambda, beta, nu, and mu carrageenans.

The lambda forms exhibit numerous sulfur groups compared to the kappa forms. The iota forms are intermediate.

The beta, mu, and nu forms occur in smaller quantities, and are regarded as impurities that diminish the gelatinizing effect of the iota and kappa forms.

The type of carrageenan retained for the present invention is the lambda type.

As compared with the iota and kappa carrageenans, the lambda carrageenans do not exhibit any syneresis effect. They exhibit no gelatinizing, but thickening properties. In contact with a solution of alkaline and/or alkaline-earth salts, however, these carrageenans yield a gelatinized mass. This reaction is instantaneous, and occurs without prior heat treatment.

Thickeners of cellular origin are extracted from culture media in which the specific microorganisms have been cultivated. Depending on the composition of the medium, these microorganisms will secrete different constituents in greater or lesser quantities. The gums that emerge from these media are:

the pullulan gums and their derivatives;
the rhamsan gums and their derivatives;
the wellan gums and their derivatives.

Like the carrageenans, these various gums have gelatinizing or thickening properties depending on the groups attached to the basic skeleton:

The rhamsan and wellan gums are obtained from an *Alcaligenes* species of microorganism. The rhamsan gums are heteropolysaccharides made up of tetrasaccharide units. The base unit comprises three D-glucose molecules joined to one another in a β(1→4) configuration, the last being joined in an α(a→4) configuration to an L-rhamnose molecule. Both rhamsan and wellan gums have a very wide variety of uses as thickening agents: they can be used in pharmaceuticals and in food products, or also in the construction sector.

The pullulan gums are secreted by *Aureosbasidium pullulans*. They are linear polymers whose main skeleton is constituted by a concatenation of maltotriose molecules joined to one another in an α(1→6) configuration. Maltotriose is made of up three glucose molecules. Thanks to the different hydroxyl groups present on the polymer, this microorganism has been made to synthesize numerous derivatives depending on the nature of its nutritional medium. These gums are once again widely used in a variety of sectors ranging from pharmaceuticals to paint production. They are very good film-producing agents, exhibiting very good elasticity.

Whatever the thickeners, of vegetable origin or obtained from the metabolism of certain microorganisms, the proportion thereof to be utilized in order to achieve the same result as with gelatin can vary from a concentration of 2% to 80% by weight, relative to the total weight of the preparation.

Each of these aforesaid substances can be used as a single "extemporaneous gelatinizer" or in combination with one or more others, such as:

lambda carrageenans/gum arabic to enhance welding during the manufacture of soft capsules, thanks to the adhesive properties of gum arabic;
lambda carrageenans/pullulan gum to modulate release of the encapsulated active ingredient;
etc.

The proportion of other "extemporaneous gelatinizers" can vary from 10% to 90% by weight, relative to the total weight of thickening agents.

Depending on the thickening agent that is utilized, the dissolution medium can be aqueous or hydroalcoholic. The proportion of the alcohol phase can vary from 10% to 90% by weight, relative to the total weight of the preparation.

Depending on the thickening agent utilized, the addition of certain ions allows better hydration of the saccharide polymer; such is the case for the lambda carrageenans.

Agents that promote solubilization of the carrageenans belong to the class of the alkaline ions and the alkaline-earth ions (sodium and potassium). These are, among others:

the sodium and potassium salts of hydrochloric, sulfuric, nitric, phosphoric, and citric acids, and derivatives; and
the hydroxides of sodium and potassium.

The proportion of alkaline and alkaline-earth ions that can be introduced into the medium varies from 0% to 50% by weight, relative to the total weight of the preparation.

The aqueous phase can be buffered, depending on the thickening agent used. "Buffered" is understood to mean an aqueous phase that is capable of absorbing variations in acid or alkaline pH depending its composition, so as to maintain a constant pH in the medium. This is even more important given that certain thickening agents are readily degraded as a function of the final pH of the medium; this is accentuated by prolonged exposure to heat. Such is the case for the lambda carrageenans which, in the present of dextrose in a neutral medium, experience a progressive hydrolysis over time that is enhanced by the effect of heat. Specifically, in a neutral medium and over a period of 24 hours, a decrease in the viscosity of the medium is observed as a result of a progressive hydrolysis of the carrageenans that releases acid radicals into the medium. In the context of acid buffer solutions, the following compositions can be the pairs:

hydrochloric acid/sodium chloride or hydrochloric acid/potassium phthalate or hydrochloric acid/glycine buffer;
citric acid/citrate or citric acid/sodium hydroxide buffer;
lactic acid/lactate buffer.

The proportion of the various components allows an acid pH (between 2 and 5) to be maintained.

In the case of the lambda carrageenans, the best stability is observed in a neutral or alkaline environment. The buffer solutions that can be used in this instance correspond to the following composition:

phosphate buffers: sodium or potassium phosphate;
carbonate buffer: bicarbonate/carbonate;
phthalate buffer: potassium diphthalate/hydrochloric acid.

The pH of the buffered medium can vary from 5 to 12.

As has been mentioned previously, the films that form part of the composition of the soft capsules must exhibit a certain elasticity in order to allow injection of the solution to be encapsulated under pressure. These substances are all the more important given that the thickening agents utilized for the implementation of gelatin-free soft capsules do not possess the intrinsic property of forming elastic films. The elasticity of the films is achieved by using plasticizing agents that belong to the class of polyols: glycerol, sorbitol, maltodextrins, dextrose, mannitol, xylitol, lactitol, propylene glycol, polyoxyethylene glycol 400 to 6000, natural and semi-synthetic glycerides, and derivatives thereof. The quantity of these substances introduced into the preparation is such that the elasticity coefficient of the film can vary from 1 to 5 (one to five times the initial length). The proportion of these plasticizing substances that can be introduced into the medium varies from 0% to 50% by weight, relative to the total weight of the preparation.

As was defined initially, the soft capsules must conform to certain characteristics regarding disaggregation time. In order to achieve these goals, a certain number of excipients can be introduced into the medium to control this parameter. Two categories of products can be employed:

surfactants;
disintegrating agents.

The surfactants facilitate wetting of the products with which they are in contact. Those used in the present invention belong to various classes of product:

Nonionic; these are:
 sorbitan esters: polysorbates, Spans, Tweens, etc.;
 polyethoxylated fatty acids: PEG 8 stearate to PEG 100 stearate;
 polyethoxylated fatty alcohols: PEG monolaurate ether mixture having 4 to 23 oxyethylene groups on the polyoxyethylene chain, etc.;
 glycol esters: methylglycol stearate;
 glycerol esters: glycerol monostearate, etc.;
 PEG esters;
 sucrose esters;
 fatty alcohol and PEG ethers: Brij;
 alkylphenol ethers and PEG ethers;
surfactants having an amide function:
 coco fatty acid monoethanolamide, lauric acid monoethanolamide, etc.;
 myristic acid diethanolamide, lauric acid diethanolamide, etc;
 lauric acid monoisopropanolamine.
Ionic; these are:
 sulfated derivatives: sodium lauryl sulfate and its derivatives;
 sulfonated derivatives: sodium dodecyl sulfosuccinate and its derivatives;
 quaternary ammoniums: cetyltrimethylammonium chloride, lauryl pyridinium chloride, distearyldimethylammonium chloride, etc.;
Amphoteric, which are: cocalkyl dimethylammonium betaine, derivatives of fatty acid amides having a betaine structure, lauryl-α-iminodiproprionic acid and its derivatives, laurylmyristyl-α-aminopropionic acid and its derivatives, etc.

The quantity of these substances introduced into the solution of the thickening agents is such that the disaggregation time can vary from 3 minutes to 8 hours. These quantities can vary from 0 to 20% by weight, relative to the total weight of the preparation. In certain cases, however, the presence of surfactants alone is not sufficient. Disintegration agents allow the disaggregation time to be improved. Numerous substances can play this role. Among them, the starches have been retained, in particular their derivatives, since they exhibit good solubility in the solubilization media for the thickening substances. The so-called "soluble" natural starches are therefore retained as a disintegrating agent in the aforesaid invention, as well as their derivative products resulting from:

physical modifications: pre-gelatinization;
chemical modifications:
 chemical or enzymatic dextrinization reactions;
 acid hydrolysis;
 oxidation reaction;
 substitution reaction with
  phosphoric acid
  adipic acid
  acetic acid
  hydroxypropyl or hydroxyethyl groups.

These various disintegration agents can be obtained from wheat, rice, corn, manioc, and potato starches. The quantities used can range from 0 to 50% by weight, relative to the total weight of the preparation. Preservation adjuvants, coloring agents, and opacifiers can also be introduced into the composition. The proportion of preservatives can vary from 0.01 to 10% by weight, relative to the total weight of the preparation. The coloring agents can be water-soluble or immobilized on aluminum lake or another support. The optimum concentration required is between 0.01% and 5% by weight for the coloring agents and 1 to 10% by weight for the opacifiers, relative to the total weight of the preparation.

The solutions thus produced have a viscosity when cold of between 200 millipascals and 1,000,000 millipascals, and a concentration of solid matter that can range from 10% to 80% by weight, relative to the final weight of the composition.

From these solutions, films can be generated having a thickness on the order of 0.5 mm to 4.0 mm at the time of casting. Gelatinization thereof, induced by the complexing agents, causes the films thus obtained to exhibit physical characteristics similar to those made of gelatin or iota carrageenans, in terms of their elasticity, thickness, disaggregation time, welding, and appearance.

The "gelatinizing agents" or complexing agents that induce extemporaneous gelatinization of the aforesaid preparations belong to two classes of product, depending on the thickening substances that are employed:

- alcohols, such as ethanol, methanol, propanol, isopropanol, butanol (in the case of gum arabic);
- the
  - calcium
  - barium
  - titanium
  - zinc
  - aluminum
  - sulfur
  - silicon salts of mineral and/or organic acids, as well as the corresponding oxides, hydroxides, and carbonates (in the case of the lambda carrageenans and the pullulan, rhamsan, and wellan gums).

In the case of the alcohols, the latter can be used pure or diluted; their concentration can vary from 10% to 90% by weight, relative to the final volume of the hydroalcoholic complexing agent solution.

In the case of the salts and the oxides acting as complexing agents, they are first dissolved

- in an acid, neutral, or alkaline aqueous medium; or
- in a hydroalcoholic medium to enhance their action.

Their concentration can vary from 1% to utilization of so-called saturated solutions.

Regardless of the acids or hydroxides used to solubilize the salts and oxides, their normality, or concentration in the aqueous medium, varies from 0.01N to 10N.

The acids retained for the present invention are:
- of mineral origin: hydrochloric, sulfuric, nitric, phosphoric, etc. acid;
- of organic origin: acetic, formic, lactic, citric, succinic, etc. acid.

The weld strength of the two films thus implemented will be a function of the degree to which they are gelatinized, and consequently of the contact time between the film and the complexing agent. Depending on the nature of the thickening agent and the complexing agent used, the contact time can vary from 10 seconds to 10 minutes.

The present invention also refers to the method for producing the mass, films, and soft capsules. Energy consumption is reduced, unlike methods currently utilized to implement soft capsules, whether from gelatin, carrageenans (kappa or iota), or thermoplastic starch. This is because, as a result of the intrinsic gelatinization of the products cited above, it is necessary to work at high temperature to prevent the gelatin and carrageenans from solidifying in the conduits. In the case of thermoplastic starches, the extruders that are used consume a great deal of energy in order to effect in situ the chemical conversion of the natural starch.

The production method that is the object of the present invention, on the other hand, is novel in that the thickening agents exhibit extemporaneous or induced gelatinizing properties, thus preventing solidification of the preparation in the conduits. The mass is prepared, in the majority of cases, under cold conditions. Heating may be necessary in order to accelerate hydration or solubilization of the thickening agents and of certain other additives. The temperatures utilized to promote hydration or solubilization never exceed 90° C. One this phase is complete, it is no longer necessary to continue heating. The mixers used for production of this mass are conventional, of the kneader/mixer type.

Once the mass has been produced, it undergoes a conventional vacuum degassing step to eliminate air, which is capable of forming bubbles during production of the films. By working under vacuum, this degassing step can be made simultaneous with manufacture of the mass. The degassed mass is transferred to the film formation systems either by simple gravity or under pressure, using either endless screws or a press.

As soon as the film has been formed, it is brought into contact with the complexing solution.

This contact can be obtained by
- immersion;
- spraying; or
- spraying/immersion.

Depending on the material employed to produce the films, immersion and/or spraying can be done simultaneously on both surfaces of the film, or alternately by spontaneous detachment of the gelatinized film. Specifically, it has been observed in the case of the lambda carrageenans that the gelatinized films, once formed, detach instantly from their support as a result of penetration, by capillary action, of the complexing solution between the film and the support, thus allowing gelatinization of the other surface.

The examples of the film manufacturing system depicted below are possible diagrams of methods to conform to the manufacturing mode defined, and do not limit them in any way.

Figure 1:
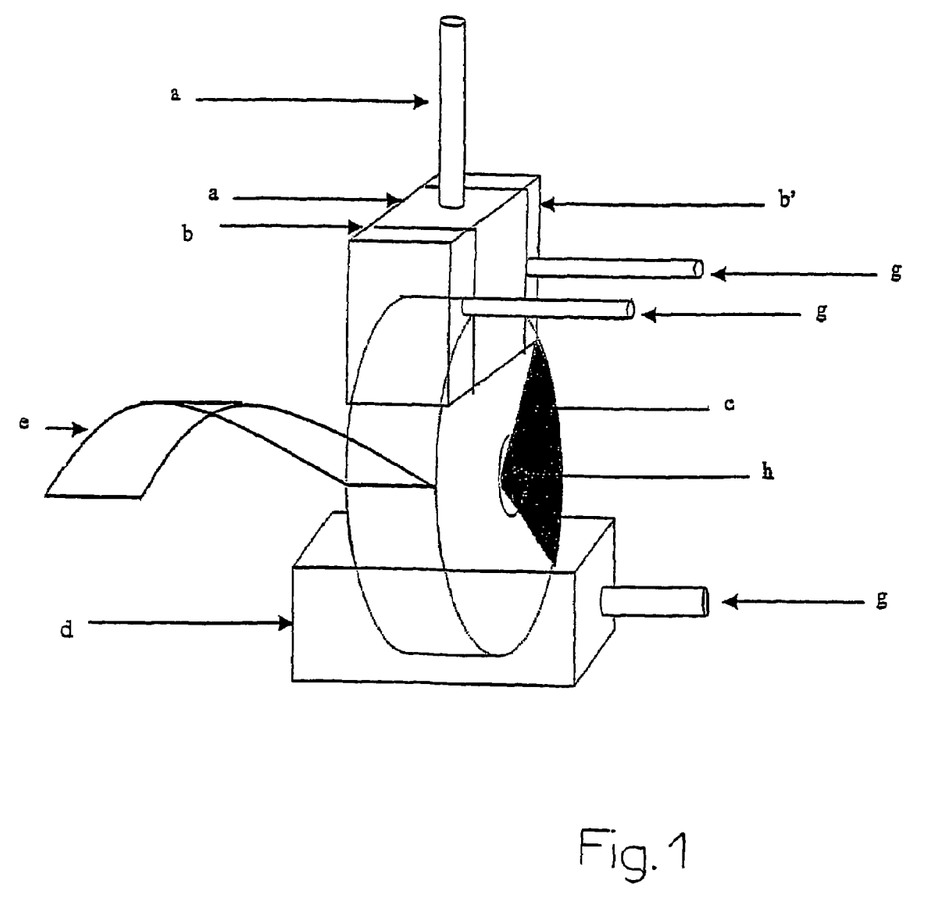
FIG. 1 is a perspective view of the drum system used to manufacture soft capsules.
Figure 2:
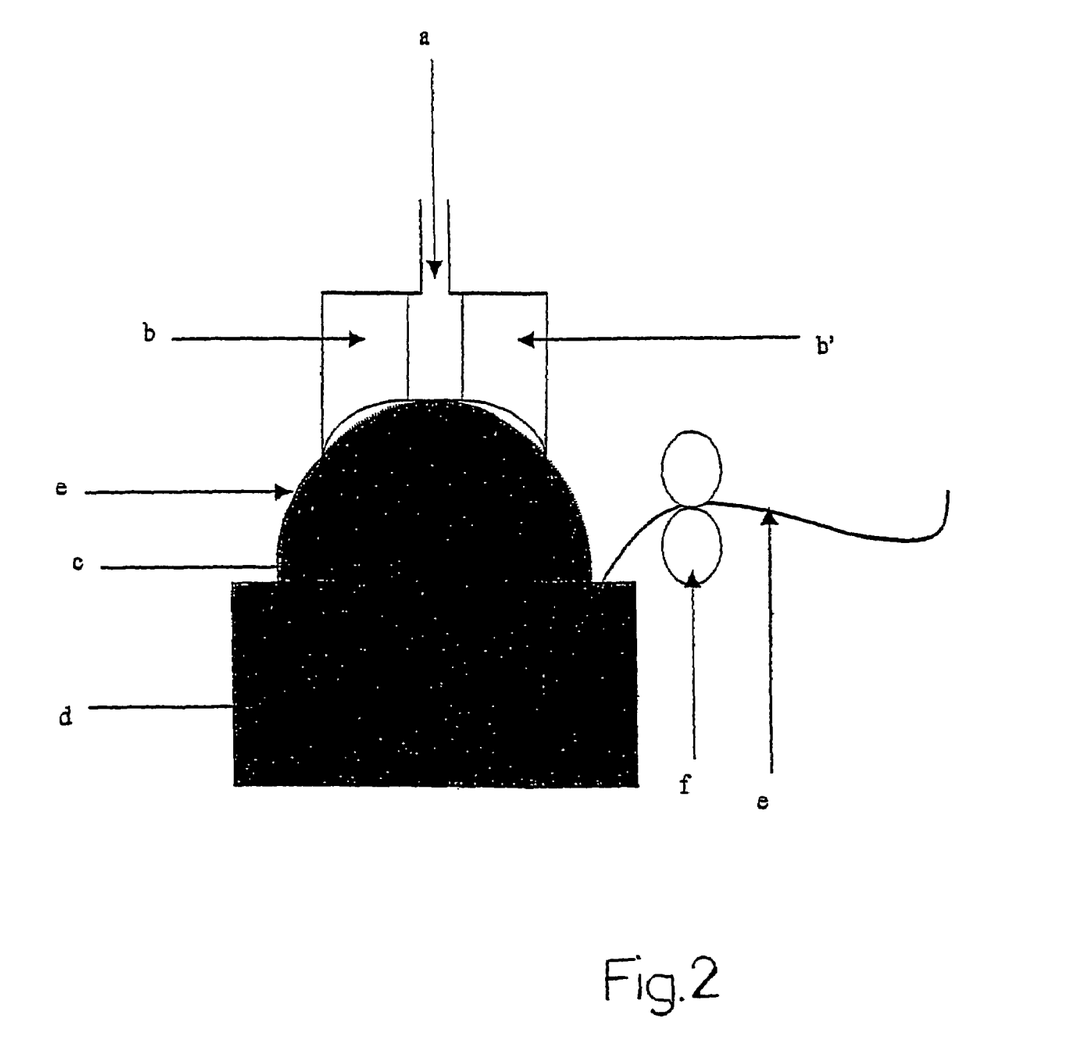
FIG. 2 is the frontal section of the drum system used to manufacture soft capsules.
Figure 3:
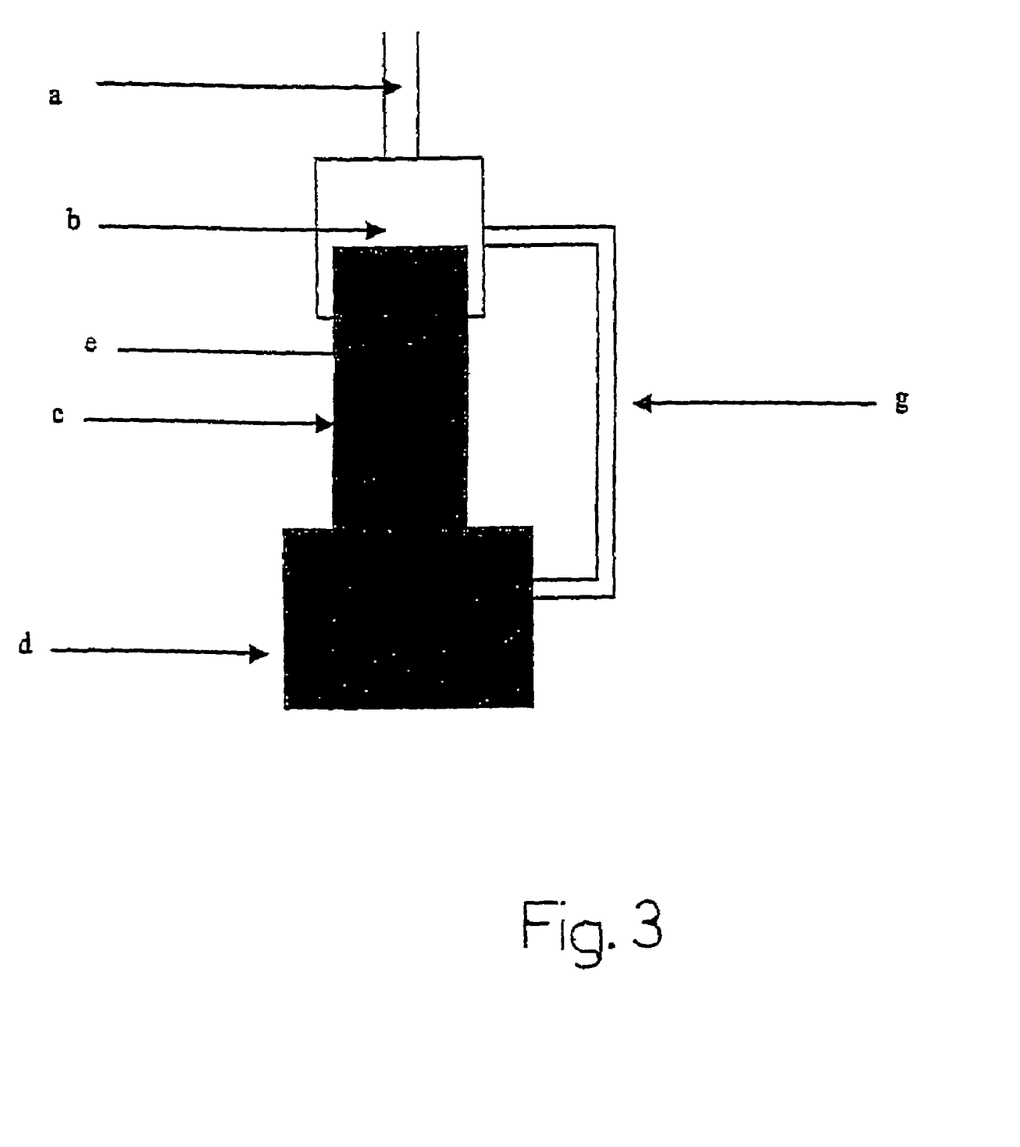
FIG. 3 is the transverse section of the drum system used to manufacture soft capsules.

FIGS. 1 to 3, which are views in perspective, in frontal section, and in transverse section respectively, illustrate the "drum system" conventionally used to manufacture soft capsules. Two injectors (b and b') have been configured in an upper position for spraying the complexing solution, as well as an immersion bath (d) to complete gelatinization of the film after detachment from the drum.

In the present case, gelatinization of the film is obtained first on one surface and then on the other.

Beginning with feed system (a), the mass that has been produced,thus yields a film (e) that is pulled by a drum (c). Beginning at nozzle (b), film (e) gelatinizes on the outer surface. Simultaneously, the complexing agent from nozzle (b') trickles along the drum and, by capillary action, causes gelatinization of the inner surface of film (e) and detachment thereof from drum (c). Depending on the height of the pulling system (labeled f and shown only in FIG. 1) for the gelatinized film, the latter can spend a shorter or longer time in immersion tank (d), as a function of the desired criteria.

Figure 4:
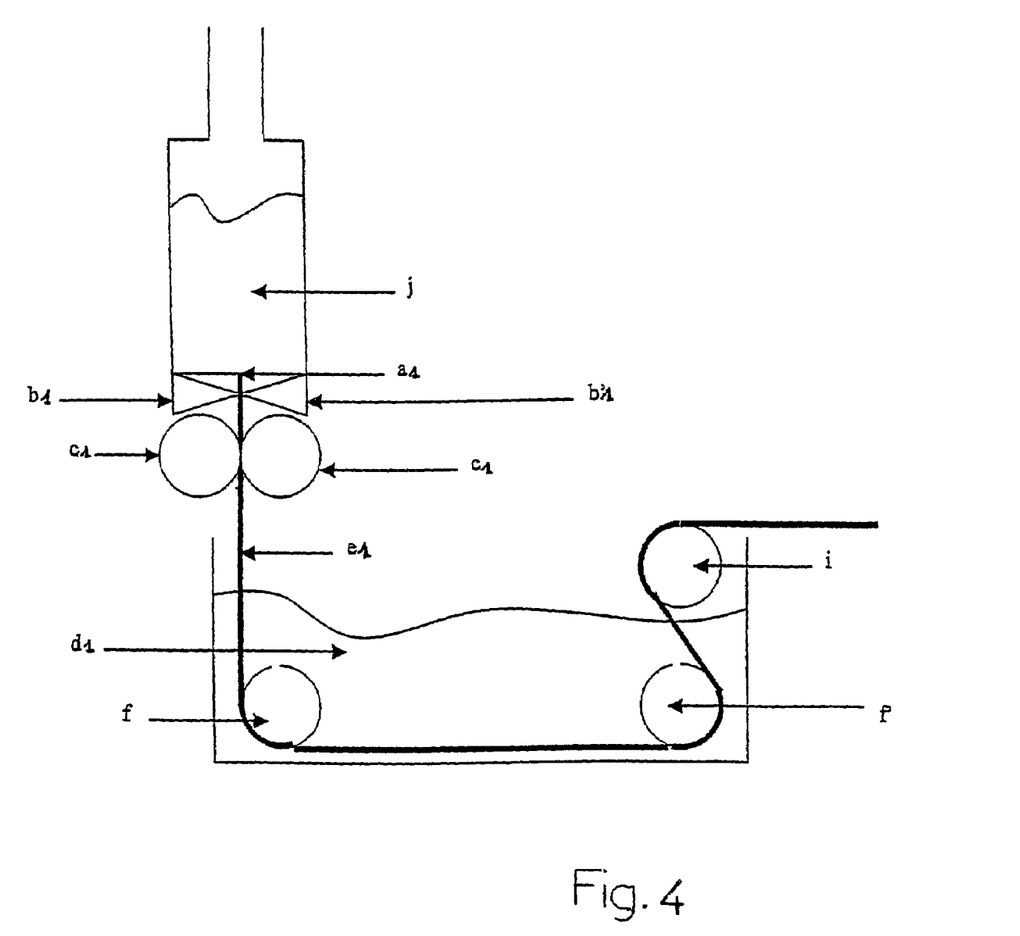
FIG. 4 is the system for instantaneous gelatinization of both surfaces of the film upon emergence from the vessel for manufacture of the mass.

The system depicted in section in FIG. 4 allows instantaneous gelatinization of both surfaces upon emergence from the vessel for manufacture of the mass. As it emerges (a1), the processed mass yields a film (e1) that is instantaneously gelatinized on both sides, as a result of spraying of the complexing solution from the two sprayers (b1) and (b1') arranged on either side of the outlet orifice (a&). A film pulling system (c1, f, f', i) allows the film to remain, or not, in an immersion bath (d1) to complete its gelatinization. The gelatinized film thus formed can be dried in an air stream whose temperature can vary from −10° C. to 70° C. during the process of transferring it toward the "encapsulation" section of the machine, as indicated in FR Patent 9710190 and U.S. Pat. No. 6,331,205.

After drying, the gelatinized films exhibit a thickness ranging between 0.2 and 2.0 mm. Their shrinkage capability after drying is between 0% and 20%.

The films thus obtained can be lubricated to facilitate transfer thereof to the encapsulation molds, which can be either rotary in the case of the RP Scherer method, or alternating in the case of the Norton method.

The lubricants that can be used are:
- conventional edible oils: peanut, sunflower, olive, etc.
- emulsifiers such as glycerol esters and polyoxyethylene glycol esters, triglycerides, propylene glycol esters, and their derivatives.

These lubricants can be used pure or diluted, with a dilution ranging from 10 to 75%.

The films thus obtained for the manufacture of soft capsules can encapsulate powders, solutions, and suspensions whose vehicles comprise a mixture, or not, of:

oils: peanut, sunflower, olive, etc., and Labrafil type oils;

polyoxyethylene glycol: PEG 400, 600, etc.;

propylene glycols;

emulsifiers: polysorbates, soy lecithin;

suspension agents such as hydrogenated oils;

aqueous solutions containing a quaternary ammonium.

During encapsulation of the aforesaid substances, the capsule closing temperature can be between 50° C. and 100° C. The capsule closing process can utilize heated molds whose temperature must be between 60° C. and 110° C.

The exemplifying embodiments of films presented below are merely possible formulae for compositions according to the invention, provided in non-limiting fashion.

EXAMPLE 1

| | |
|---|---|
| Gum arabic | 40 g |
| Glycerin | 10 g |
| Water to make | 100 g |

EXAMPLE 2

| | |
|---|---|
| Lambda carrageenans | 10.0 g |
| Sodium chloride | 3.0 g |
| Glycerin | 10.0 g |
| Water to make | 100 g |

Complexing solution: 50% calcium chloride solution

EXAMPLE 3

| | |
|---|---|
| Lambda carrageenans | 10.00 g |
| Sodium chloride | 3.00 g |
| Glycerin | 15.00 g |
| Orange Yellow S | 0.05 g |
| Water to make | 100.00 g |

Complexing solution: 50% calcium chloride solution

EXAMPLE 4

| | |
|---|---|
| Lambda carrageenans | 10.00 g |
| Sorbitol | 20.00 g |
| Polysorbate 80 | 1.50 g |
| Water to make | 100.00 g |

Complexing solution: 50% calcium chloride solution

EXAMPLE 5

| | |
|---|---|
| Lambda carrageenans | 10.00 g |
| Potassium chloride | 2.00 g |
| Glycerin | 15.00 g |
| Polysorbate 80 | 1.50 g |
| Sodium methyl parahydroxybenzoate | 0.12 g |
| Sodium propyl parahydroxybenzoate | 0.03 g |
| Water to make | 100.00 g |

Complexing solution: 50% calcium chloride solution

EXAMPLE 6

| | |
|---|---|
| Lambda carrageenans | 39.500 g |
| Sodium chloride | 1.918 g |
| Glycerin | 30.00 g |
| Polysorbate 80 | 6.000 g |
| Sodium methyl parahydroxybenzoate | 0.36 g |
| Sodium propyl parahydroxybenzoate | 0.09 g |
| Monosodium phosphate | 0.390 g |
| Disodium phosphate | 7.320 g |
| Water to make | 300.00 g |

Complexing solution: 50% calcium chloride solution

EXAMPLE 7

| | |
|---|---|
| Lambda carrageenans | 39.500 g |
| Glycerin | 30.00 g |
| Hydroxypropyl starch | 60.000 g |
| Sodium methyl parahydroxybenzoate | 0.36 g |
| Sodium propyl parahydroxybenzoate | 0.09 g |
| Monosodium phosphate | 0.390 g |
| Disodium phosphate | 7.320 g |
| Water to make | 300.00 g |

Complexing solution: 50% calcium chloride solution

EXAMPLE 8

| | |
|---|---|
| Lambda carrageenans | 39.500 g |
| Sodium chloride | 1.918 g |
| Sorbitol | 30.00 g |
| Maltodextrin | 40.000 g |
| Sodium methyl parahydroxybenzoate | 0.36 g |
| Sodium propyl parahydroxybenzoate | 0.09 g |
| Monosodium phosphate | 0.390 g |
| Disodium phosphate | 7.320 g |
| Water to make | 300.00 g |

Complexing solution: 50% calcium chloride solution

Based on Example 7, 163.00 kg of water, the monosodium phosphate, the disodium phosphate, and the preservatives are introduced into a 500-liter double-walled stainless-steel tank, and stirring is continued until the ingredients are completely dissolved. The temperature of the preparation is gradually raised to 90° C. to facilitate hydration of the hydroxypropyl starch upon its introduction into the medium. After homogenization, the glycerin is added along with the lambda carrageenans. The temperature is maintained at 90° C. for 3 to 4 hours to allow complete hydration of the lambda carrageenans. The mass produced in this fashion can be stored for more than 48 hours at 25° C.

After degassing of the preparation, it is transferred to the encapsulation machines at a minimum temperature of 50° C.

By simple gravity or by pressure, formation of the following occurs (depending on the film production method):
- a deposit of mass on the drums, whose temperature is on the order of 10-15° C.; or
- a thick, non-gelatinized film upon emergence from the feed opening between two cylinders, whose temperature is on the order of 10-15° C.

Gelatinization of the film is then obtained by spraying the 50% calcium chloride solution, depending on the film production method:
- either onto the drum surface, the outer side of the film, then the inner;
- or by spraying each side of the film.

Regardless of the film manufacturing method, after gelatinization the film is transferred directly to the encapsulation section after passing (or not) into the immersion bath for a period of 30 seconds to 1 minute. The resulting film undergoes drying in an air stream whose temperature is controlled to between +4° C. and 30° C. The soft capsules are produced by hot-sealing the films after lubrication,
- either with the method that is conventionally used, i.e. prior heating of the film to between 70° C. and 100° C. before pressure welding;
- or by heating the molds to a temperature between 70° C. and 100° C.

The invention claimed is:

1. A process for manufacturing a gelatinized film for soft capsules, the process comprising:
   a) dissolving a thickening agent under mixing and cold conditions, the thickening agent having an instant gelatinizing property upon contact with complexing agent solutions, in aqueous or hydroalcoholic medium buffered or not, to form a viscous mass;
   b) solubilizing additives under mixing and cold or hot conditions in the viscous mass;
   c) vacuum degassing the viscous mass to eliminate the air from the viscous mass;
   d) transferring the viscous mass to a film formation system;
   e) forming a film from the viscous mass on drum systems at a temperature of about 10-15° C. to form a viscous film;
   f) instantaneously gelatinizing the viscous film by spraying or dipping, or both, in a complexing agent solution, to form a gelatinized film; and
   g) drying the gelatinized film through an air stream having a temperature comprised between −10° C. to 70° C.

2. A process for manufacturing films for soft capsules according to claim 1, wherein the at least one thickening agent is selected from the group consisting of arabic gums and their derivatives, lambda carrageenan, and pullulan gums and their derivatives.

3. A process for manufacturing films for soft capsules according to claim 1, wherein the concentration of the at least one thickening agent is between 2% and 80% by weight, relative to the final weight of the preparation.

4. A process for manufacturing films for soft capsules according to claim 1, wherein the thickening agent comprises a combination of two or more thickening agents.

5. A process for manufacturing films for soft capsules according to claim 1, wherein the dissolution medium is a hydroalcoholic medium, and wherein the proportion of the alcohol for thickening agent dissolution in the hydroalcoholic medium varies from 10% to 90% by weight, relative to the total weight of the dissolution medium.

6. A process for manufacturing films for soft capsules according to claim 1, the dissolution medium further comprising at least one sodium or potassium salt to increase solubilization of the at least one thickening agent.

7. A process for manufacturing films for soft capsules according to claim 6, wherein the proportion of the sodium or potassium salt varies from 0 to 50% by weight, relative to the final weight of the preparation.

8. A process for manufacturing films for soft capsules according to claim 1, wherein the aqueous phase of the dissolution medium has a pH varying from 2 to 12.

9. A process for manufacturing films for soft capsules according to claim 1, wherein the pH of the dissolution medium is controlled with buffered solutions selected from the group consisting of hydrochloric acid/sodium chloride, hydrochloric acid/potassium phthalate, hydrochloric acid/glycine, citric acid/citrates, citric acid/sodium hydroxide, lactic acid/lactate, monosodium phosphate/disodium phosphate, monopotassium phosphate/dipotassium phosphate, bicarbonate/carbonate, and potassium diphthalate/hydrochloric acid.

10. A process for manufacturing films for soft capsules according to claim 1, wherein the additives comprise at least one polyol plasticizer selected from the group consisting of glycerol, sorbitol, maltodextrins, dextrose, mannitol, xylitol, lactitol, propylene glycol, polyoxyethylene glycol 400 to 6000, natural and semi synthetic glycerides, and their derivatives.

11. A process for manufacturing films for soft capsules according to claim 10, wherein the proportion of the at least one polyol plasticizer varies from 0 to 50% by weight, relative to the total weight of the preparation.

12. A process for manufacturing films for soft capsules according to claim 1, wherein the additives comprise at least one surfactant selected from the group consisting of ionic surfactants, non ionic surfactants, and amphoteric surfactants.

13. A process for manufacturing films for soft capsules according to claim 12, wherein the concentration of surfactant content varies from 0 to 20% by weight, relative to the total weight of the preparation.

14. A process for manufacturing films for soft capsules according to claim 1, wherein the additives comprise at least one disintegrating agent, associated or not with surfactants, the at least one disintegrating agent being a soluble starch selected from the group consisting of potato starch, corn starch, rice starch, manioc starch and wheat starch derivatives, the derivatives having been or not chemically or/and physically modified.

15. A process for manufacturing films for soft capsules according to claim 14, wherein the at least one disintegrating agent comprises between 0 and 50% by weight, relative to the total weight of the preparation.

16. A process for manufacturing films for soft capsules according to claim 1, wherein the concentration of solid material in the encapsulating mass is between 10% and 80% by weight, relative to the final weight of the composition.

17. A process for manufacturing films for soft capsules according to claim 1, wherein the film complexing agent solution is a saline solution of a mineral or organic acid, a hydroalcoholic solution, or a mixture of a saline solution of a mineral or organic acid and a hydroalcoholic solution.

18. A process for manufacturing films for soft capsules according to claim 17, the film complexing solution being a hydroalcoholic solution, wherein the hydroalcoholic complexing solution contains ethanol, methanol, propanol, isopropanol, or butanol.

19. A process for manufacturing films for soft capsules according to claim 17, the film complexing agent solution being a hydroalcoholic solution, wherein the hydroalcoholic solution contains between 10% and 90% of alcohol by weight, relative to the final volume of the hydroalcoholic complexing solution.

20. A process for manufacturing films for soft capsules according to claim 17, the film complexing agent solution being a saline solution, wherein the saline complexing solution includes at least one ion selected from the group consisting of calcium ion, barium ion, titanium ions, zinc ion, aluminum ions, sulfur ions, and silaceous ions salt of mineral and organic acid, and hydroxides.

21. A process for manufacturing films for soft capsules according to claim 17, the film complexing agent solution being a saline solution, wherein the concentration of salt in the saline complexing solution ranges from 1% to the saturation of the solution.

22. A process for manufacturing films for soft capsules according to claim 1, wherein the ungelled film is in contacted with the complexing solution by spraying complexing solution onto the ungelled film, dipping the ungelled film into the complexing solution, or both.

23. A process for manufacturing films for soft capsules according to claim 1, wherein the gelatinization process in contact with the complexing solution agent varies between 10 seconds and 10 minutes.

24. A process for manufacturing films for soft capsules according to claim 1, further comprising drying the gelled film in an air stream at a temperature between −10° C. and +70° C.

25. A process for manufacturing films for soft capsules according to claim 1, further comprising sealing the gelled film under pressure and at a temperature between 50° C. and 100° C.

26. A process for manufacturing films for soft capsules according to claim 1, further comprising encapsulating an aqueous and/or oily solution with the gelled film.

\* \* \* \* \*